United States Patent [19]

Cantrell

[11] Patent Number: 4,663,306

[45] Date of Patent: * May 5, 1987

[54] PYRIDINE-SOLUBLE EXTRACT-REFINED DETOXIFIED ENDOTOXIN COMPOSITION AND USE

[75] Inventor: John L. Cantrell, Corvallis, Mont.

[73] Assignee: Ribi ImmunoChem Research, Inc., Hamilton, Mont.

[*] Notice: The portion of the term of this patent subsequent to Mar. 13, 2001 has been disclaimed.

[21] Appl. No.: 535,037

[22] Filed: Sep. 23, 1983

[51] Int. Cl.$^4$ ............... A61K 37/00; A61K 39/00; A61K 39/02; A61K 35/78
[52] U.S. Cl. .................................. 514/2; 530/352; 530/359; 530/403; 530/407; 530/806; 530/825; 424/88; 424/92; 424/195.1; 435/68
[58] Field of Search ................ 424/92, 93, 85, 88, 424/195, 177, 180; 435/68, 70; 260/112 R; 514/2; 530/352, 359, 403, 407, 806, 825

[56] References Cited

U.S. PATENT DOCUMENTS 4,014,992 4/1977 Jolles et al. .................... 424/92
4,374,827 2/1983 Sindo et al. .................... 424/92
4,436,728 3/1984 Ribi .............................. 424/177

OTHER PUBLICATIONS

Cantrell et al, *Cancer Research*, v. 39 pp. 3954-3963, Sep. 1979.
Ribi et al, *Cancer Immun. Immun.*, v. 7 pp. 43-58, 1979.

Primary Examiner—Thomas G. Wiseman
Assistant Examiner—Robin L. Teskin
Attorney, Agent, or Firm—Burgess, Ryan & Wayne

[57] ABSTRACT

A pharmaceutical composition comprising a purified pyridine-soluble extract of a microorganism and a refined detoxified endotoxin which is effective in producing an immunological response in warm blooded animals and humans. Methods of using the composition for these purposes are also disclosed.

18 Claims, No Drawings

PYRIDINE-SOLUBLE EXTRACT-REFINED DETOXIFIED ENDOTOXIN COMPOSITION AND USE

BACKGROUND OF THE INVENTION

The present invention is directed to a pharmaceutical composition containing refined detoxified endotoxin (RDE) in combination with a pyridine-soluble extract of a microorganism (PE). The RDE used in the present composition is characterized as having no detectable 2-keto-3-deoxyoctanoate, between about 350 and 475 nmoles/mg of phosphorus and between about 1700 and 2000 nmoles/mg of fatty acids. The PE contains between about 3 and 20% by weight of protein, about 10 to 40% by weight of sugar, and about 35 to 60% by weight of fatty acids. The composition is effective to obtain remission and/or regression of cancerous tumors in warm-blooded animals.

Bacteria such as *Corynebacterium parvum* have been the subject of experimental work to isolate and characterize the component responsible for inducing inhibition of tumor growth [see for example, *Anti Tumor Activity and Lymphoreticular Stimulation Properties of Fractions Isolated from C. parvum;* Cantrell, et al, Cancer Research 39, pgs. 3554–3563 (September, 1979)]. Apart from anti-tumor activity, *C. parvum* is a potent stimulator of the lymphoreticular system resulting in undesirable increases in spleen and liver weights and blastogenesis. It has been discovered that a pyridine-soluble extract of a microorganism such as *C. parvum* possesses potent anti-tumor properties without the undesirable toxic effects associated with the prior art products.

Endotoxic extracts obtained from Enterobacteriacae including parent organisms and mutants are known. These extracts have been used for immunotherapy of various immunogenic tumors [see, *Peptides as Requirement for Immunotherapy of the Guinea-Pig Line-10 Tumor with Endotoxins;* Ribi, et al, Cancer Immunol. Immunother. Vol. 7, pgs. 43–58 (1979) incorporated herein by reference]. However, the endotoxin extracts are known to be highly toxic and, therefore, of limited use in the treatment of cancerous tumors. Efforts have been made to "detoxify" the endotoxins while retaining its tumor regressive capacity. As shown in Ribi, et al, chemical procedures known to detoxify endotoxins while retaining adjuvanticity, such as succinylation and phthalylation resulted in both loss of endotoxicity and tumor regressive potency. Therefore, prior art attempts to obtain an endotoxin product having high tumor regressive potency and little or no toxicity have thus far not been successful.

SUMMARY OF THE INVENTION

It is, therefore, an object of the present invention to provide a pharmaceutical composition containing a pyridine-soluble extract of a microorganism in combination with a refined detoxified endotoxin.

It is another object of the invention to provide a method of treating tumors in warm blooded animals and humans using the composition containing the pyridine-soluble extract of a microorganism and the refined detoxified endotoxin.

The Pyridine-soluble Extract of a Microorganism (PE)

The PE contains between about 3 and 20% by weight of protein, about 10 to 40% by weight of sugar, and about 35 to 60% by weight of fatty acids in combination with *C. parvum* whole cells, and preferably contains about 5% by weight of protein, about 35% by weight of sugar and about 55% by weight of fatty acids.

As used herein, there is no limitation with respect to the use of a sugar; all sugars can be used. The same holds true with respect to fatty acids; there is no limitation with respect to the fatty acids which can be used.

The protein comprises amimo acids and ammonia and the amino acids include, for example, the following; (there was utilized in these determinations, a Beckman amino acid analyzer:)

| | |
|---|---|
| Asparginine | 0.273 |
| Threonine | 0.108 |
| Serine | 0.585 |
| Muramic acid | 0.219 |
| Glutamic acid | 0.267 |
| Glycine | 0.39 |
| Alanine | 0.173 |
| Diamino pimelic acid | 0.444 |
| Isoleucine | 0.121 |
| Leucine | 0.167 |
| Phenylalanine | 0.034 |
| Histidine | 0.088 |
| Lysine | 0.544 and |
| Ammonia | 0.524 |

The amounts expressed above are in terms of weight percent and the total protein is 6.34% by weight.

Any microorganism may be used to obtain the pyridine-soluble extract including, for example, *M. bovis* BCG, *M. phlei, M. smegmatis, M. kansasii, Nocardia rubra, Nocardia asteroides, Proprionibacterium acnes* Type II, and *Corynebacterium parvum. Corynebacterium parvum* and *Proprionibacterium acnes* Type II are especially preferred.

Whole cells of the microorganism, preferably in the form of a paste, are mixed with pyridine. The resulting mixture is separated to obtain a supernatant fraction which contains the pyridine-soluble extract and a pyridine residue. Optionally, the pyridine residue may be subjected to repeated separation procedures as described above using pyridine to remove further quantities of the desired extract.

The pyridine is then removed from the extract and the dried extract is dialyzed against a suitable liquid such as distilled water. The absence of whole cells or cell fragment contaminants is confirmed by electron microscopy. The resulting purified extract may then be lyophilized by known methods to obtain a stable product.

The pyridine-soluble extract produced in accordance with this invention is combined with RDE to produce a composition having potent anti-tumor activity without stimulating the induction of spleen and liver enlargements. If the pyridine soluble extract is suspended in water, the suspension can be separated into an aqueous soluble and an aqueous insoluble fraction. The aqueous soluble extract is most desirable since it can be easily injected parenterally while at the same time retaining tne anti-tumor activity of the pyridine extract. The tumors which may be treated by this composition include animal tumors such as bovine squamous cell carcinoma, bovine fibrosarcoma, equine sarcoid, equine melanoma, equine squamous cell carcinoma, canine mammary tumors, canine adenoma and canine melanoma and human tumors such as breast tumors, lung tumors, colon tumors, malignant melanoma, squamous cell carcinomas, ovarian tumors, uterine tumors, bladder and head and neck tumors.

The Refined Detoxified Endotoxin (RDE)

Endotoxin extracts of the type used as a starting material to produce RDE may be obtained from any Enterobacteriaciae including parent ogranisms and mutants. By way of example, the following genera are illustrative of the type of microorganisms that may be used: Salmonella, Shigella, Escherichia, Brucella, Bordetella, Citrobacter, Pseudomonas, Pasturella, Neisseria, Proteus, Klebsiella, and Serratia.

The following species are typically employed: *S.minnesota, S.typhimurium, B.pertussis, B.abortus, S.enteritidis, E.coli, S,typhi, S.marcescens, S.typhosa, Shingella flexni*, and *S.abortus equi.*

The endotoxic extracts used as a starting material may be prepared by one of several known methods [see, for example, (1) Webster, M. E., Sagin, J. F., Landy, M., and Johnson, A. G., *J. Immunol.* 1955, 744,55.

(2) Westphal, O., Luderitz, O., and Bister, F., *Z. Naturforsch*, 76 148 (1952).

(3) Westphal, O., Pyrogens, *Polysaccharides in Biology, Tr. Second Macy Conference* (George F. Springer, ed.), Madison, N.J. Madison printing Co., 1957, 115.

(4) Galanos, C., Luderitz, O., Westphal, O., *Eur. J. Biochem,* 9 245 (1969)

(5) Chen, C. H., Johnson, A. G., Kasai, N., Key, B. A., Levin, J., Nowotny, A., *J. Infect. Dis* 128 543 (1973).

(6) Ribi, E., Haskins, W. T., Landy, M., Milner, K. C., *The Journal of Experimental Medicine* 114 647 (1961).

(7) Leive, L., *Biochem. Biophys. Res. Comm.* 21 290 (1965).

(8) Ribi, E., Milner, K. C., and Perrine, T., *J. Immunol.* 82 75 (1959].

The preferred method of obtaining the endotoxic extract is that disclosed by Chen et al; namely, methanol-chloroform precipitation.

The methanol-chloroform precipitate (MCP) is then reacted with an organic or inorganic acid and then lyophilized to produce a hydrolyzed crude lipid A with reduced toxicity and pyrogenicity as compared with the starting endotoxin material. This material is then treated with a solvent which is capable of specifically dissolving fatty acids and other impurities without dissolving the crude lipid A. The phosphate content of the detoxified, refined lipid A is about one-half that observed for toxic endotoxin suggesting that the phosphate content is related to the toxic effects of endotoxins.

The preferred inorganic acids used to react with MCP are hydrochloric acid, sulfuric acid, or phosphoric acid and the preferred organic acids are toluene sulphonic acid or trichloroacetic acid. The reaction may suitably be conducted at a temperature between about 90° and 130° C., for a time sufficient to complete hydrolysis, usually between about 15 and 60 minutes.

The preparation of crude detoxified endotoxin may be accomplished by reacting the starting material with the acid in the presence of an organic solvent such as chloroform, methanol, and ethanol or combinations thereof.

The resulting crude lipid A is suspended in acetone which is the preferred solvent for dissolving the fatty acids and other impurities. The solvent is then removed to produce crude detoxified endotoxin.

The crude detoxified endotoxin is then dissolved in a solvent and the solution is passed through a suitable chromatographic column such as a molecular exclusion chromatographic column, to separate the RDE fractions which are then combined after removal of the solvent. The crude detoxified endotoxin solution is passed through a Sephadex column in the presence of a solvent such as chloroform, methanol, acetone, pyridine, ether or acetic acid or combinations thereof. The pressure of the column may vary but is typically in the range of between about atmospheric and 100 lbs/in$^2$ and the flow rate is between about 0.1 and 10 ml/min.

The crude detoxified endotoxin solution may be passed through a DEAE-cellulose column under the same pressure conditions as mentioned above for the Sephadex column. The flow rate is maintained between about 2 and 15 ml/min. The solvents used are also the same as used for the Sephadex column although water and/or diethylamine can be added to all mixtures at a concentration of up to about 1%.

Other methods of producing RDE from crude detoxified endotoxin include passing the solution through a low pressure silica-gel 60 column having a particle size of between about 25 and 63 microns and using a solvent comprised of chloroform, methanol, water and ammonium hydroxide. The preferred volume ratio of the components of the solvent is about 50:25:4:2.

The refined detoxified endotoxin (RDE) has no detectable 2-keto-3-deoxyoctanoate, between about 350 and 475 nmoles/mg of phosphorus and between about 1700 and 2000 nmoles/mg of fatty acid.

DESCRIPTION OF PREFERRED EMBODIMENTS

The composition is administered by injection in a pharmaceutically acceptable medium such as an oil-droplet emulsion or a physiologic saline solution, and is preferably administered directly into the tumor under conditions more particularly described below. Administration can be by IV injection, or by IV infusion.

The composition may be stabilized, as, for example, by a lyophilization procedure and then reconstituted without loss of potency.

The amount of RDE in a single injection for treatment of animals is between about 25–500 micrograms/ml, suitably between 50 and 100 micrograms/ml. and the amount of PE is between about 25–500 and suitably between about 100 and 250 micrograms/ml.

The number of milliliters of the biologic injected into the tumor is determined by the size of the tumor in accordance with the following table:

| Animal Dosage According to Tumor Size | |
| --- | --- |
| Diameter of Tumor (cm) | Amount of Biologic Injected (ml) |
| 0–1 | up to 0.5 |
| 1–2 | 0.5 to 2.5 |
| 2–3 | 2.5 to 5 |
| 3–5 | 5 to 10 |
| 5–8 | 10 to 15 |
| greater than 8 | 15 to 20 |

The maximum dose per injection is about 10 milligrams of RDE and about 25 of PE. The course of treatment comprises up to 4 to 10 injections administered at about two week intervals.

The present composition in a suitable injection medium such as physiologic saline solution is administered directly into human tumors. The amount of RDE in a single injection is between about 5 and 1,000 micrograms, suitably between about 25 and 500 micrograms. The amount of PE is between about 50 and 5,000 micrograms, suitably between about 200 and 3000 micrograms. The preferred dosage level for RDE is about 100 micrograms and for PE it is about 1000 micrograms. All of the above-mentioned dosage levels are based on a typical 70 kilogram adult patient. The injections are administered about once every week for up to a total of about 15 injections.

As mentioned above, the composition for treatment of warm blooded animals and humans may be used in the form of a saline or an oil droplet emulsion. The amount of oil used is in the range of between about 0.5 and 3.0 percent by volume based on the total volume of the composition. It is preferred to use between about 0.75 and 1.5 percent by volume of the oil. Examples of such oils include light mineral oil, squalane, 7-n-hexyloctadecane, Conoco superoil and Drakeol 6 VR mineral oil (produced by the Pennreco Company, Butler, Pa.

The homogenized oil containing mixture is then combined with a detergent which may optionally be dissolved in a saline solution prior to mixing. The amount of detergent is typically between about 0.02 and 0.20 percent by volume and preferably between about 0.10 and 0.20 percent by volume based on the total volume of the composition. Any common detergent material may be used including Tween-80, and Arlacel (produced by the Atlas Chemical Company).

The mixture resulting from the addition of detergent is then homogenized to form a suspension which has a high percentage of oil droplets coated with the active components as determined by observation under a microscope.

The following examples are for illustrative purposes only and are not intended to limit or in any way redefine the invention as claimed in the claims appended hereto.

EXAMPLE 1

Preparation of Pyridine-Soluble Extract from *Proprionibacterium acnes* Type II (Strain VPI 0204)

*Proprionibacterium acnes* Type II (Strain VPI 0204) was grown and harvested at 37° C. in NIH thioglycolate broth for between 48 and 72 hours to obtain a whole cell paste. The paste was then washed with 500 ml of distilled water. 90 grams (wet weight) of the washed paste was mixed with 200 ml. of neat pyridine and centrifuged at 1700×g for one hour at 4° C. A pyridine-soluble extract was removed as a supernatant fraction. The remaining residue was extracted with additional pyridine under identical conditions as described above. Following filtration, using Whatman No. 1 Paper, the pyridine extracts were pooled and the solvent was removed by evaporation at 50° C. in a Buchi Rotavapor (Brinkmann Instruments, Westbury, N.Y. The dried pyridine extract was extensively dialyzed against distilled water and then lyophilized. The resulting purified pyridine extract contained about 5% by weight of protein, about 35% by weight of sugar and about 55% by weight of fatty acids. The extract was examined under an electron microscope and found to be free of contaminating whole cells and cell wall fragments. The yield of the pyridine-soluble extract was 9% (1.62 g. based on approximate dry weight).

EXAMPLE 2

Preparation of Pyridine-Soluble Extract *M.bovis* Strain BCG

*M. bovis* strain BCG was grown and harvested in Sautons medium at 37° C. for between 3-4 weeks to obtain a washed whole cell paste. 50 grams (wet weight) of the washed paste was then treated in the same manner as Example 1 to produce a yield of the pyridine-soluble extract of 7% (3.5 g). The extract contained 15% by weight of protein, 10% by weight of sugar and 52% by weight of fatty acids.

EXAMPLE 3

Preparation of Aqueous Extract 500 mg of pyridine extract obtained by the procedure of Example 1 was sonicated in 100 ml. of distilled water for 15-30 minutes. The resulting suspension was centrifuged at 12,000 rpm in an RC2B centrifuge at 4° C. for 40 minutes. The supernatant was decanted and saved. The residue was extracted two more times, as above. The supernatants were combined in a lyophilizing bottle, shell frozen and lyophilized. Yield 230 mg (46%).

EXAMPLE 4

Preparation of Crude Detoxified Endotoxin

A 650 mg sample of a methanol-chloroform precipitate produced in accordance with the procedure of Chen, et al *J. Infect. Dis.* 128 543 (1973) was suspended in 150 ml of 0.1N HCl, in a three necked round bottom flask fitted with a condenser, and immersed in a sonicator. After sonication for about 30 minutes, the glass apparatus was then lowered into an oil bath maintained at 120° C. which allowed the interior temperature of the flask to approach or exceed the boiling point of the solution. Superheating of the solution was minimized by fitting the flask with a capillary tube attached to a nitrogen gas source through one of the necks. A continuous flow of nitrogen was maintained throughout the hydrolysis procedure.

Hydrolysis was continued for 30 minutes, and then the solution was cooled in an ice bath, sonicated to disperse the solid material and distributed in corex tubes. The flask was washed with distilled water to remove all solid material adhering to the sides of the flask, and the wash was added to the suspension in the corex tubes. Centrifugation was carried out at 12,000 rpm for 80 minutes. The supernatant was decanted and discarded. The solid residue was resuspended in distilled water, sonicated until the suspension was well dispersed and recentrifuged. The centrifugation process was then repeated. The residue was taken up in distilled water, shell frozen and lyophilized yielding 382 mg of crude lipid A. 150 mg of this material was treated with cold (0° C.) acetone to remove fatty acids, sonicated, and filtered through a Whatman No. 1 gravity filtration apparatus at 5° C. 100 mg of crude detoxified endotoxin remained after drying.

EXAMPLE 5

Preparation of Crude Detoxified Endotoxin

A 120 mg sample of MCP (methanol-chloroform precipitate) was suspended in 12 ml of absolute methanol, sonicated to disperse solid materials and distributed into 6 (1×10 cm) screw cap vials. 2 ml of 0.2N HCl were added to each tube and the resulting suspension was incubated in a boiling water bath for 45 minutes. After hydrolysis, the tubes were cooled in an ice water bath and centrifuged for about 10 minutes at 2500 rpm. The supernatant was decanted and 5 ml of a 2:1 chloroform/methanol mixture were added to the residue to effect dissolution. 2 ml of water were added per tube and the solution was mixed. The biphasic solution was recentrifuged at 2500 rpm for 10 minutes. The upper water phase was discarded and 1 ml of a 4:1 chloroform/methanol mixture was added to each tube resulting in a clear solution. The solutions were pooled, and the solvent evaporated on a rotary evaporator. The residue was dried under high vacuum and lyophilized to yield 45 mg of crude lipid A. 20 mg of this material were treated with cold (0° C.) acetone, sonicated, and filtered through a Whatman No. 1 gravity filtration apparatus at 5° C. 13 mg of crude detoxified endotoxin remained after drying.

EXAMPLE 6

Preparation of Refined Detoxified Endotoxin 110 g LH-20-100 (25-100 micron particle size: Pharmacia) were combined with 600 ml of a 2:1 chloroform/methanol mixture which was permitted to stand for 30 minutes. The resulting slurry was added to a 25×1000 mm glass chromatography column (BRL Laboratories) fitted with pressure fittings. After packing was completed, the column was attached by means of Teflon pressure tubing to an ISCO Model 132 pump. 400 ml of a 4:1 chloroform/methanol mixture were pumped through the column at the rate of 3 ml/min. 100 mg of crude detoxified endotoxin prepared in accordance with Example 4 were applied to the column in 2.5 ml of a 4:1 chloroform/methanol mixture via a sample loop. The flow was reduced to 1 ml/min. and after 150 ml of eluant were collected, the effluent was connected to a fraction collector. 4 ml fractions were collected and refined detoxified endotoxin fractions were determined by thin layer chromatographic analysis of the fractions [E. Merck, 0.25 mm thick, chloroform/methanol/-$H_2O$/$NH_4OH$ (50:25:4:2) as eluant].

The refined detoxified endotoxin fractions were combined and the solvent evaporated leaving 30 mg of refined detoxified endotoxin as a white powder.

EXAMPLE 7

Preparation of Refined Detoxified Endotoxin 33 g of DEAE-cellulose (Whatman DE-32) were suspended in 150 ml of glacial acetic acid and agitated gently for 10 minutes to obtain a slurry powder. The mixture was set aside overnight.

The slurry was poured into a 25×400 mm column, allowed to settle with tapping, and excess acid was thereafter drained. The column was washed with 2000 ml of methanol followed by 200 ml of a 4:1 chloroform/methanol mixture. A 100 mg sample of crude detoxified endotoxin produced in accordance with Example 4 was added to the column in 3 ml of a 4:1 chloroform/methanol mixture or an 80:20:1 mixture of chloroform, methanol and water. The column was eluted with 350 ml of a 4:1 chloroform/methanol mixture followed by 300 ml of a 99:1 methanol/water mixture. Using a linear gradient apparatus, the column was eluted with 2000 ml of a linear gradient starting with 100% methanol and ending with 0.2M acetic acid in methanol. The column was eluted at the rate of 6 ml/min. and 15 ml fractions were collected. Every other fraction was analyzed for total phosphorous content according to the procedure of Bartlett, G. R., *J. Biol. Chem.* 234, 466–471 (1959). The fractions were pooled and evaporated on a rotary evaporator to near dryness and taken up in 10 ml of a 2:1 chloroform/methanol mixture and 40 ml of 0.001M acetic acid in a separatory funnel. The lower layer was separated, filtered through Whatman No. 2 filter paper and evaporated to dryness to yield 19.2 mg of refined detoxified endotoxin.

EXAMPLE 8

23 eight to ten week old female C3HeBFeJ mice were injected intraperitoneally with $10^5$ ovarian teratocarcinoma cells. After 24 hours, five mice were injected once with 0.2-0.5 ml of an isotonic saline solution containing 50 micrograms of RDE and six mice were injected once with 0.2-0.5 ml of the saline solution containing 300 micrograms of PE and 50 micrograms of RDE. Finally, twelve mice were injected once with 0.2-0.5 ml of the saline solution as a control. After 21 days, 4 of the 5 mice injected with RDE showed complete regression of the tumor and 6 of 6 of the mice injected with RDE and PE showed similar results. On the other hand, 10 of 12 mice of the control group died by the twenty-first day and the remaining two still showed evidence of the cancer cells.

EXAMPLE 9

Forty-five 8-10 week old female C3HEJ mice were injected with $10^5$ ovarian teratocarcinoma. After 24 hours, 15 of the mice were injected once with 0.2-0.5 ml of an isotonic saline solution containing 1400 micrograms of PE and 15 of the mice were injected once with 0.2-0.5 ml of the saline solution containing 300 micrograms of PE and 50 micrograms of RDE. Finally, 15 mice were injected once with 0.2-0.5 ml of the saline solution as a control. After 30 days, 5 of the 15 mice injected with PE were still living and 8 of the 15 mice injected with RDE and PE had shown tumor regression and were still living. On the other hand, 14 of the 15 mice of the control group had died with the remaining 1 mouse showing tumor regression.

What is claimed is:

1. A therapeutic composition comprising a therapeutically effective amount of:
   (a) a purified pyridine-soluble extract obtained from a microorganism selected from the group consisting of *M. bovis* BCG, *M. phlei*, *M. smegmatis*, *M. kansasii*, *Nocardia rubra*, *Nocardia asteroides*, *Proprionibacterium acnes* Type II, and *Corynebacterium parvum*, said extract containing between about 3 and 20% by weight of protein, between about 10 and 40% by weight of sugar, and between about 35 and 60% by weight of fatty acids, and having been prepared by the steps of:
      (1) preparing a whole cell paste of said microorganism;
      (2) washing said paste;
      (3) treating said paste with pyridine to produce an extract and a residue;
      (4) removing said pyridine from said extract; and
      (5) dialyzing said dried extract to obtain purified pyridine-soluble extract;
   (b) refined detoxified endotoxin having no detectable 2-keto-3-deoxyoctanoate and having between 375 and 475 nmoles/mg of phosphorus and between about 1700 and 2000 moles/mg of fatty acids; and having been prepared by the steps of:

(1) hydrolyzing an endotoxin extract derived from Enterobacteriaciae with an acid capable of hydrolyzing the same;
(2) lyophilizing the hydrolyzed product to obtain crude lipid A;
(3) treating crude lipid A with a first solvent capable of dissolving fatty acids contained therein to remove said fatty acids from a resulting insoluble product;
(4) dissolving the resulting insoluble product in a second solvent capable of dissolving the same; and
(5) passing the resulting solution through a chromatographic column of a type which will allow elution of the desired product to obtain the refined detoxified endotoxin; and (c) a pharmaceutically acceptable carrier.

2. The composition of claim 1, wherein said microorganism is *Corynebacterium parvum*.

3. The composition of claim 1, wherein said microorganism is *Proprionibacterium acnes* Type II.

4. The composition of claim 1, wherein said extract contains about 12% by weight of each of protein and sugar and about 45% by weight of fatty acids.

5. The composition of claim 1, wherein the ratio of said extract to said refined detoxified endotoxin is from 1:1 to 100:1.

6. The composition of claim 5, wherein the amount of said extract is between about 50 and 5000 micrograms and the amount of said refined detoxified endotoxin is between about 5 and 1000 micrograms.

7. The composition of claim 6, wherein the amount of said extract is about 500 micrograms and the amount of said refined detoxified endotoxin is about 100 micrograms.

8. The composition of claim 1, wherein said composition is in lyophilized form.

9. The composition of claim 1, wherein said carrier is physiological saline solution.

10. The composition of claim 1, wherein said composition is in the form of an oil droplet emulsion.

11. The composition of claim 10, wherein said oil is selected from the group consisting of light mineral oil, squalane, squalene, and 7-n-hexyloctadecane.

12. The composition of claim 10, wherein said oil is present in an amount between about 0.5 and 3.0% by volume based on the total volume of the composition.

13. The composition of claim 10, further comprising a detergent in an amount between about 0.02 and 0.25% by volume based on the total volume of the composition.

14. A method for imparting immunotherapy in a warm blooded animal having an immunogenic tumor comprising injecting into said warm blooded animal a therapeutically effective amount of a therapeutic composition comprising:
(a) a purified pyridine-soluble extract obtained from a microorganism selected from the group consisting of *M. bovis* BCG, *M. phlei, M. smegmatis, M. kansasii, Nocardia rubra, Nocardia asteroides, Proprionibacterium acnes* Type II, and *Corynebacterium parvum*, said extract containing between about 3 and 20% by weight of protein, between about 10 and 40% by weight of sugar, and between about 35 and 60% by weight of fatty acids, and having been prepared by the steps of:
(1) preparing a whole cell paste of said microorganism;
(2) washing said paste;
(3) treating said paste with pyridine to produce an extract and a residue;
(4) removing said pyridine from said extract; and
(5) dialyzing said dried extract to obtain purified pyridine-soluble extract;
(b) refined detoxified endotoxin having no detectable 2-keto-3-deoxyoctanoate and having between 375 and 475 nmoles/mg of phosphorus and between about 1700 and 2000 moles/mg of fatty acids; and having been prepared by the steps of:
(1) hydrolyzing an endotoxin extract derived from Enterobacteriaciae with an acid capable of hydrolyzing the same;
(2) lyophilizing the hydrolyzed product to obtain crude lipid A;
(3) treating crude lipid A with a first solvent capable of dissolving fatty acids contained therein to remove said fatty acids from a resulting insoluble product;
(4) dissolving the resulting insoluble product in a second solvent capable of dissolving the same; and
(5) passing the resulting solution through a chromatographic column of a type which will allow elution of the desired product to obtain the refined detoxified endotoxin; and (c) a pharmaceutically acceptable carrier.

15. The method of claim 14, wherein said composition is injected parenterally or directly into said immunogenic tumor for up to 15 injections.

16. The method of claim 15, wherein said injections are made at intervals of at least one week.

17. A therapeutic composition comprising a therapeutically effective amount of:
(a) a purified pyridine-soluble extract obtained from a microorganism selected from the group consisting of *M. bovis* BCG, *M. phlei, M. smegmatis, M. kansasii, Nocardia rubra, Nocardia asteroides, Proprionibacterium acnes* Type II, and *Corynebacterium parvum*, said extract containing between about 3 and 20% by weight of protein, between about 10 and 40% by weight of sugar, and between about 35 and 60% by weight of fatty acids, and having been prepared by the steps of:
(1) preparing a whole cell paste of said microorganism;
(2) washing said paste;
(3) treating said paste with pyridine to produce an extract and a residue;
(4) removing said pyridine from said extract; and
(5) dialyzing said dried extract to obtain purified pyridine-soluble extract;
(b) refined detoxified endotoxin having no detectable 2-keto-3-deoxyoctanoate and having between 375 and 475 nmoles/mg of phosphorus and between about 1700 and 2000 moles/mg of fatty acids; and having been prepared by the steps of:
(1) hydrolyzing at a temperature between about 90° and 130° C. for at least 15 minutes, an endotoxin extract derived from Enterobacteriaciae with an acid capable of hydrolyzing the same; said acid being selected from the group consisting of hydrochloric, sulfuric, phosphoric, toluene sulfonic and trichloroacetic acid;
(2) lyophilizing the hydrolyzed product to obtain crude lipid A;

(3) treating crude lipid A with acetone to dissolve fatty acids contained therein and to remove said fatty acids from a resulting insoluble product;
(4) dissolving the resulting insoluble produce in a solvent selected from the group consisting of chloroform, methanol, acetone, pyridine, ether, acetic acid, water, ammonium hydroxide and mixtures thereof, which solvent is capable of dissolving the same; and
(5) passing the resulting solution through a Sephadex, DEAE-cellulose or low pressure silica-gel chromatographic column which will allow elution of the desired product and recovering the refined detoxified endotoxin; and
(c) a pharmaceutically acceptable carrier.

18. A method for imparting immunotherapy in a warm blooded animal having an immunogenic tumor comprising injecting into said warm blooded animal a therapeutically effective amount of a therapeutic composition comprising:
(a) a purified pyridine-soluble extract obtained from a microorganism selected from the group consisting of *M. bovis* BCG, *M. phlei*, *M. smegmatis*, *M. kansasii*, *Nocardia rubra*, *Nocardia asteroides*, *Proprionibacterium acnes* Type II, and *Corynebacterium parvum*, said extract containing between about 3 and 20% by weight of protein, between about 10 and 40% by weight of sugar, and between about 35 and 60% by weight of fatty acids, and having been prepared by the steps of:
(1) preparing a whole cell paste of said microorganism;
(2) washing said paste;
(3) treating said paste with pyridine to produce an extract and a residue;
(4) removing said pyridine from said extract; and
(5) dialyzing said dried extract to obtain purified pyridine-soluble extract;
(b) refined detoxified endotoxin having no detectable 2-keto-3-deoxyoctanoate and having between 375 and 475 nmoles/mg of phosphorus and between about 1700 and 2000 moles/mg of fatty acids; and having been prepared by the steps of:
(1) hydrolyzing at a temperature between about 90° and 130° C. for at least 15 minutes, an endotoxin extract derived from Enterobacteriaciae with an acid capable of hydrolyzing the same; said acid being selected from the group consisting of hydrochloric, sulfuric, phosphoric, toluene sulfonic and trichloroacetic acid;
(2) lyophilizing the hydrolyzed product to obtain crude lipid A;
(3) treating crude lipid A with acetone to dissolve fatty acids contained therein and to remove said fatty acids from a resulting insoluble product;
(4) dissolving the resulting insoluble product in a solvent selected from the group consisting of chloroform, methanol, acetone, pyridine, ether, acetic acid, water, ammonium hydroxide and mixtures thereof, which solvent is capable of dissolving the same; and
(5) passing the resulting solution through a Sephadex, DEAE-cellulose or low pressure silica-gel chromatographic column which will allow elution of the desired product and recovering the refined detoxified endotoxin; and
(c) a pharmaceutically acceptable carrier.

* * * * *